United States Patent [19]

Bazzano

[11] Patent Number: 5,137,888
[45] Date of Patent: Aug. 11, 1992

[54] N,N- SUBSTITUTED AMINES AND USE THEREOF IN HAIR GROWTH PROMOTION

[76] Inventor: Gail S. Bazzano, 4506 Avron Blvd., Metairie, La. 70006

[21] Appl. No.: 499,514

[22] Filed: Jun. 27, 1990

Related U.S. Application Data

[63] Continuation-in-part of Ser. No. 156,568, Feb. 17, 1988, abandoned, which is a continuation-in-part of Ser. No. 138,048, Dec. 28, 1987, abandoned, which is a continuation-in-part of Ser. No. 847,910, Nov. 27, 1985, abandoned.

[51] Int. Cl.$^5$ ............... A01N 43/58; A01N 43/60; A61K 31/495; A61K 31/50
[52] U.S. Cl. ............... 514/250; 514/252; 514/253; 514/254; 514/255; 514/257; 514/258; 514/262; 514/267; 514/277; 514/299; 514/315; 514/332; 514/333; 514/359; 514/408; 514/422; 514/229.5
[58] Field of Search ............... 544/14, 248, 255, 312, 544/323, 358, 359, 364, 374, 382; 514/229.5, 248, 249, 250, 252, 253, 254, 255, 256, 257, 258, 262, 267, 277, 299, 315, 332, 333, 359, 408, 422

[56] References Cited

U.S. PATENT DOCUMENTS 4,139,619 2/1979 Chidsey, III ............ 424/45
4,596,812 6/1986 Chidsey, III ............ 514/256

OTHER PUBLICATIONS

Catto et al. "2,4-Diamino-6-Piperidinil e 6-Piperazinilpirimidine 3-Ossido-, Nuovi Analoghi Del Minossidile" Boll. Chim. Farm. 121 (1982) pp. 16-26.

Primary Examiner—Nathan M. Nutter
Attorney, Agent, or Firm—Panitch, Schwarze, Jacobs & Nadel

[57] ABSTRACT

Novel compounds are provided having the general formula $RB_n$ wherein R is a multi-functional amine moiety having at least n amine-functional nitrogen sites, n equals 2 to about 8, and B are disubstituted heterocyclic N-oxide moieties which are attached to amine functional nitrogen atoms of R, and each B is independently selected from the group consisting of pyridines, pyrimidines and triazines. These novel compounds and similar known compounds are useful in the promotion of hair growth by topical application to mammalian skins. Particularly preferred compounds of the invention are those in which the B moieties are disubstituted with amine groups adjacent the N-oxide position of the heterocyclic ring.

20 Claims, No Drawings

N,N- SUBSTITUTED AMINES AND USE THEREOF IN HAIR GROWTH PROMOTION

CROSS-REFERENCE TO RELATED APPLICATIONS

This application is a continuation-in-part (through PCT Application US88/04690, filed Dec. 28, 1988) of my prior application Ser. No. 156,568, filed Feb. 17, 1988, now abandoned, which in turn was a continuation-in-part of my prior application Ser. No. 138,048, filed Dec. 28, 1987, now abandoned, which is a continuation-in-part if Ser. No. 847,910 now abandoned.

FIELD OF THE INVENTION

This invention relates to novel compositions of matter and methods of their preparation, as well as to known compounds which have now been surprisingly discovered to be useful as hair growth enhancers. These compounds are useful in mammals (e.g. humans and domestic animals) for promotion of hair growth.

BACKGROUND OF THE INVENTION

Various preparations have heretofore been proposed for the treatment of male pattern baldness. It is also a matter of common knowledge, however, that none of the so-called "hair growth formulae" have proven to be very efficacious.

In contrast to most epithelial structures, the hair follicle does not grow continuously throughout its life, but passes through a cycle called the pilar cycle. The pilar cycle comprises essentially three phases—namely, the anagen or growth phase during which hair is produced, normally lasting about three to seven years; the catagen phase when growth stops and the follicle atrophies, lasting about three to four weeks; and the telogen phase, which is a rest period for the follicle during which the hair progressively separates and finally falls out, and normally lasting about three to four months. Normally 80 to 95 percent of the follicles are in the anagen phase, less than 1 percent being in the catagen phase, and the rest being in the telogen phase. Whereas the telogen phase hair is uniform in diameter with a slightly bulbous, non-pigmented root, the anagen phase hair has a large colored bulb at its root.

Alopecia results when the pilar cycle is disturbed, resulting in excessive hair loss. The most frequent phenomenon is a shortening of the hair growth phase due to cessation of cell proliferation. This results in an early onset of the catagen phase, and consequently a large number of hairs in the telogen phase during which the follicles are detached from the dermal papillae, and the hairs fall out. This shortening of the growth or anagen phase of the pilar cycle may have different origins, among which are very diverse pathological origins such as febrile conditions, mental stresses, hormonal problems (such as androgenetic alopecia due to male hormones) and secondary effects of drugs. Alopecia may also be due to age and to a slowing down of mitotic activity. This dysfunction of the biological mechanism of hair growth leading to alopecia may be regarded as a disease. While there are other causes of alopecia such as greasy or oily scalp due to seborrhea and the dandruff accompanying it, the present invention is not directed to treating these extraneous causes of alopecia, but rather to treating the organic dysfunction of the hair follicle.

Minoxidil, a potent antihypertensive, is well known in the literature as a hair growth promoting agent (see U.S. Pat. Nos. 3,461,461; 3,973,016; and 3,464,987). However, it has many undesirable systemic side effects. When the topical compound is absorbed, the systemic side effects include fluid retention, tachycardia, dyspnoea, gynaecomastia, fatigue, nausea and cardiotoxicity.

There is presently a search for analogs, derivatives or other compounds of the minoxidil type which would still possess hair growth activity without the undesirable systemic effects associated with minoxidil. My prior published PCT patent applications Ser. No. US85/00556 (WO85/04577) and US85/01329 (WO86/00616) describe certain pyrimidine oxides (oxamates and carbamates) which are similar to minoxidil and have been found to be useful in hair growth promotion.

BRIEF SUMMARY OF THE INVENTION

This invention provides novel compounds as well as known compounds which have been discovered to have important hair growth promoting properties, particularly increasing and stimulating hair growth on mammalian skins, prolonging the anagen phase of the hair cycle, and converting vellus hair to growth as terminal hair, but which have much less toxicity and antihypertensive properties as compared to minoxidil.

According to the present invention, novel compounds have been found of the formula:

$$RB_n \qquad (I)$$

wherein R is a multifunctional amine moiety having at least n amine-functional nitrogen sites, n equals 2 to about 8, and B are disubstituted heterocyclic N-oxide moieties which are attached to amine-functional nitrogen atoms of R, and each B is independently selected from the group consisting of pyridines, pyrimidines and triazines, but when R is

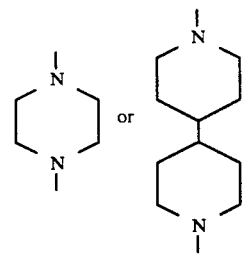

at least one B is not 2,4-diaminopyrimidine-3oxide.

Moreover, it has been unexpectedly found that the above novel compounds, as well as the two known compounds specifically excluded from the above formula, are useful in increasing the rate of hair growth on mammalian skins by applying to the skin an effective amount of a composition containing the compound. The hair growth promotion compositions of the invention may also contain a retinoid.

DETAILED DESCRIPTION OF THE PREFERRED EMBODIMENTS

The present invention provides an important advance in the search for compounds which will be more effective for promotiong hair growth, and can be used topically at higher concentrations than is possible with minoxidil. As used herein, when referring to the promotion of hair growth or increasing the rate of hair growth, it will be understood that one of more of the following is meant: increasing the rate of hair growth on the scalp; stimulating hair follicles of the skin; prolonging the anagen phase of the hair cycle; converting vellus hair to growth as terminal hair; and/or treating alopecias caused by organic dysfunction of the hair follicle.

As indicated by Formula I above, the novel and known compounds of the present invention are formed by the union of two or more N-oxide moieties or subunits represented by the letter B united by a single amine moiety represented by the letter R to form a compound which has more than one N-oxide site per molecule. Thus, it is believed that the N-oxide site is a primary active site in compounds capable of promoting hair growth.

Many of the N-oxide subunits are known per se in the art and are described particularly as parts of molecules useful in the treatment of hypertension. Such compounds include the N-oxide pyrimidines, which are described for example in U.S. Pat. No. 3,461,461; 3,973,016; and 3,464,987, and British Patent 1,486,682. N-oxide pyridines are disclosed for example in U.S. Pat. No. 4,021,562. Further, the two known compounds of Formula I, namely wherein R is a piperazinyl or bis-piperidinyl group, n is 2 and both B are 2,4-diaminopyrimidine-3-oxide, are described in A. Catto, et al., "2,4 Diamino-6-Piperidinil e 6-Piperazinilpirimidine 3-Ossido, Nuovi Analoghi Del Minossidile" Boll. Chim. Farm., 121:16-26 (1982). However, in this article, these two compounds are described only as useful in the treatment of hypertension, and not in the promotion of hair growth.

The amine moieties which may be used as R in Formula I are those derived from a number of different amines having two or more amine-functional sites, preferably on two or more amine-functional nitrogen atoms. The amine-functional nitrogen atoms may be primary or secondary amines so that when reacted with the heterocyclic N-oxide compounds to add the B moieties, secondary or tertiary amines are formed. In general, the compounds of the present invention are formed using the two or more nucleophilic hetero atom sites on acyclic, aliphatic amines; on aliphatic, carbocyclic amines; on polycyclic and aromatic amines; and on other mono- and disubstituted amines having two or more sites for reaction.

In general, examples of R amine moieties include the classes of aliphatic amines, cycloaliphatic amines, aromatic amines, heterocyclic amines and polyamines, each having two or more unsubstituted nitrogen sites, and preferably two or more nitrogen atoms with unsubstituted sites. The amines may also be substituted or unsubstituted at other nitrogen, carbon or hetero atom sites. Specific but non-limiting examples of suitable R amine moieties include the following (carbon hydrogens have been omitted in many examples for clarity):

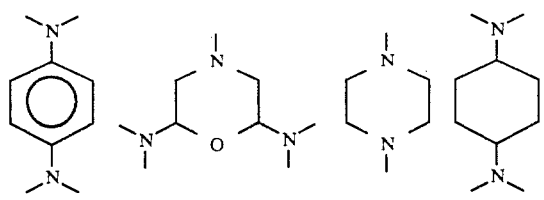

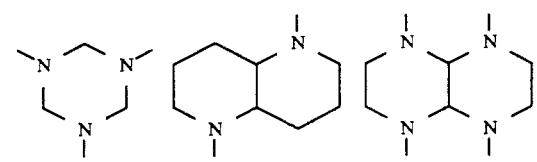

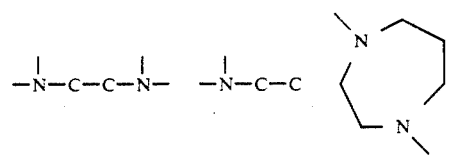

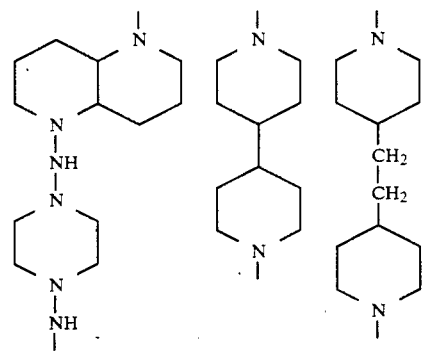

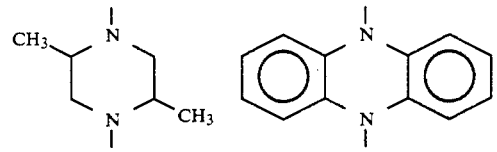

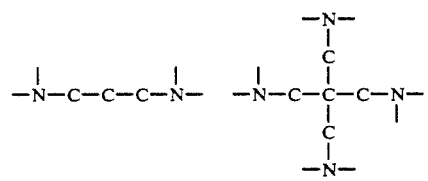

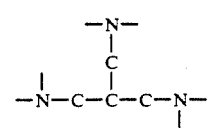

-continued

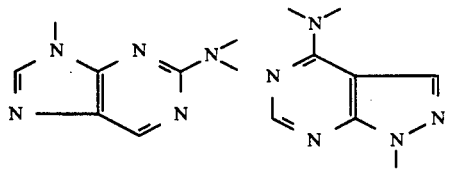
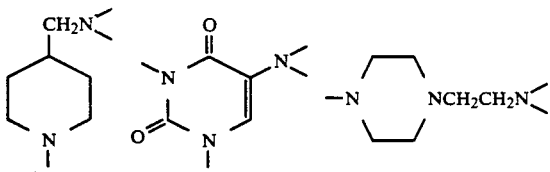
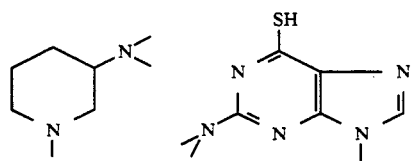
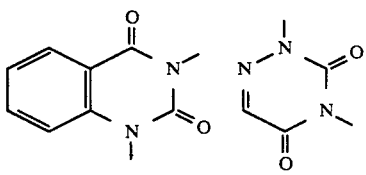
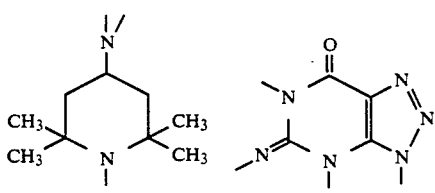
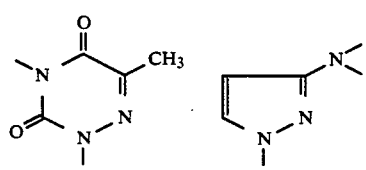
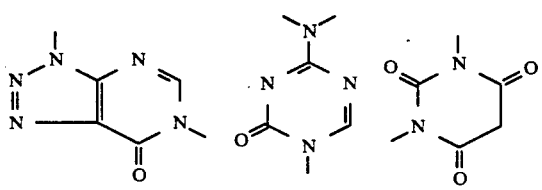

-continued

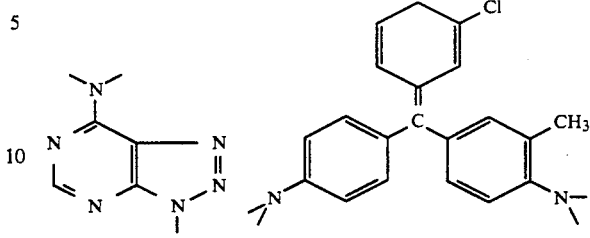

It will be understood that, in the above R moieties, the unattached bonds from the nitrogen atoms may be attached to either B groups (i.e., N-oxide moieties) or A groups which may be, for example, hydrogen or substituted or unsubstituted alkyl, cycloalkyl, alkoxy, halo, haloalkyl., haloalkoxy, haloaryl, alkenyl or aryl groups, wherein the substituents on these groups may be alkyl, halo or alkoxy. Preferably, the A groups are either hydrogen or lower alkyl, but other substituents include, for example, lower alkenyl, lower alkoxyalkyl, lower cycloalkyl, lower aryl, lower alkaryl, lower aralkyl, lower alkaralkyl, lower alkoxyaralkyl, lower haloaralkyl, lower alkylphenylthio, and halophenylthio. As used herein, the term "lower" means $C_{1-8}$ for aliphatic substituents and $C_{6-16}$ for aromatic substituents.

In the above formulas for exemplary R moieties, at least two, and preferably two to about five of the unattached nitrogen bonds are connected to B moieties, and the remainder are attached to A groups as defined above. Preferably, only one B moiety is attached to each nitrogen atom, but it will be understood that two B moieties could be attached to an amine-functional nitrogen atom where that is sterically possible. It will also be understood that the B moieties on a given R moiety of Formula I may be independently selected, and need not be the same on a given R moiety, so that different B moieties may be present in a given compound.

The B moieties useful in the compounds of Formula I are generally described as di-substituted heterocyclic N-oxide moieties, which are similar to those present in minoxidil and its analogs. Such N-oxide moieties may be represented by the following formula:

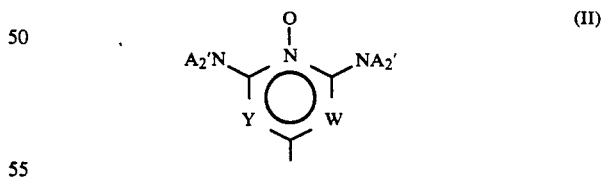

(II)

wherein W and Y are nitrogen or carbon atoms and may be the same or different; each A' may be independently selected from the same group as the A group described above, particularly hydrogen or substituted or unsubstituted alkyl, cycloalkyl, alkenyl or aryl, and may be additionally selected from carboxyacyl; R' may be A' or $NA'_2$ wherein A' is as described above. The unattached bond at the ring position para to the N-oxide group is the position for attachment of the B moiety to the R moiety of Formula I.

Exemplary compounds of the present invention are illustrated as follows:

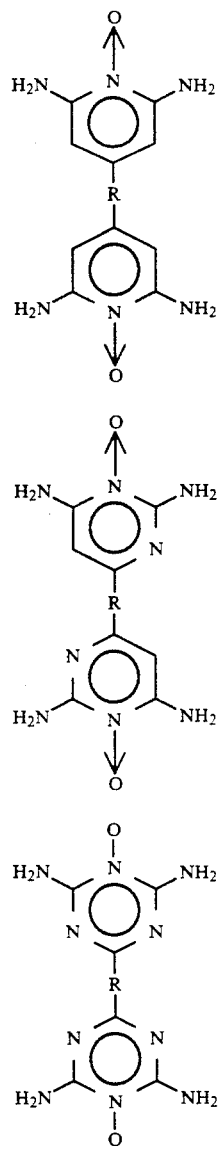

Thus, where Y and W are both carbon, the heterocylic B moieties have a single nitrogen atom in the ring and may be referred to as pyridines; where one of Y and W is carbon and the other is nitrogen, the heterocyclic rings have two nitrogen atoms and may be referred to as pyrimidines; and where Y and W are both nitrogen, the heterocyclic rings have three nitrogen atoms and may be referred to as triazines.

As shown in the above exemplary Formulas (1), (2) and (3), both A' groups are preferably hydrogen and R' is preferably $NH_2$. Other preferred substituents on the heterocyclic N-oxide B moieties are amines substituted with carboxyacyl groups. Examples of such pyrimidine B moieties are described in my published PCT patent applications Ser. No. US85/00556 (WO85/04577) and US85/01329 (WO86/00616), the disclosures of which are incorporated herein by reference. In such B moieties, R' equals $NA'_2$, and one of the A' groups on each amine substituent is hydrogen, while the other is a carboxyacyl group. The carboxyacyl groups may be, for example:

$$-\overset{O}{\underset{\|}{C}}-\text{O-methyl}; \quad -\overset{O}{\underset{\|}{C}}-\text{O-ethyl}; \quad -\overset{O}{\underset{\|}{C}}-\text{O-butyl};$$

$$-\overset{O}{\underset{\|}{C}}-\text{O-i-butyl}; \quad -\overset{O}{\underset{\|}{C}}-\text{O-benzyl}; \quad -\overset{O}{\underset{\|}{C}}-\text{O-2-methoxy-ethyl}$$

in which case the substituents are referred to as carbamates, or the carboxyacyl groups may be, for example:

$$-\overset{O}{\underset{\|}{C}}-\overset{O}{\underset{\|}{C}}-\text{O-methyl}; \quad -\overset{O}{\underset{\|}{C}}-\overset{O}{\underset{\|}{C}}-\text{O-ethyl}; \quad -\overset{O}{\underset{\|}{C}}-\overset{O}{\underset{\|}{C}}-\text{O-butyl};$$

$$-\overset{O}{\underset{\|}{C}}-\overset{O}{\underset{\|}{C}}-\text{O-i-butyl}; \quad -\overset{O}{\underset{\|}{C}}-\overset{O}{\underset{\|}{C}}-\text{O-benzyl};$$

$$-\overset{O}{\underset{\|}{C}}-\overset{O}{\underset{\|}{C}}-\text{O-2-methoxy-ethyl}$$

in which case the substituents are referred to as oxamates.

While compounds (1), (2) and (3), as well as Formula (II) set forth above, are shown in the standard unsaturated ring form it will be understood that the tautomeric forms of the compounds in which an amino substituent adjacent to the N-oxide group becomes an imino substituent are also included, as well as the solvated forms of the compounds.

The novel compounds of the invention, as well as the known compounds useful in the methods of the invention, can be formed by generally straightforward processes either known in the art or which will be evident to those of ordinary skill in the art. For example, halogenated compounds of Formula II, wherein the substituent para to the N-oxide group is a chlorine or bromine atom, for example, may be reacted with hydrides of the R moieties, i.e., compounds in which the R moieties have hydrogen atoms on the nitrogen bonds to which the B moieties are to be attached. Preferably, the compounds are reacted in the presence of an unreactive solvent, such as o-xylene, with at least a slight excess of the R moiety compound which is required for a stoichiometric reaction with the B moiety compound. A typical synthesis example is as follows:

Slightly less than a 2:1 ratio of 4-chloro-2,6-diaminotriazine-1-oxide is reacted with piperazine in the presence of o-xylene at the reflux temperature (110° C.) of the o-xylene for two hours. The resulting crystalized solid is then washed with a solution of 10% NaOH to wash out the byproduct HCl and any excess piperazine. The solid is then filtered and recrystalized with hot ethanol. The resultant yellowish precipitate obtained has a melting point greater than 280° C. with decomposition. Combustion analysis and molecular weight measurement by mass spectrum confirmed the structure as that of compound (3) above, namely N,N-bis[4-(2,6-diamino-n-oxotriazinyl)]piperazine, where R is a piperazine moiety.

Where it is desired to form carboxyacylates, e.g., carbamates or oxamates of these compounds, the reaction product described above can be reacted with a suitable carboxyacylating agent.

Although substantially any carboxyacylating agent can be used to produce these carboxyacylates, especially suitable are the anhydrides, mixed anhydrides and acid chlorides of alkanoic, cycloalkanoic, alkenoic, cycloalkenoic, aralkanoic, aromatic and heterocyclic carboxylic acids. These anhydrides and acid chlorides can also have substituents on any carbon except the carbonyl carbon with any of a wide variety of atomic or molecular moieties unreactive with the amine groups on the B moieties. Examples of such substituents are alkyl, e.g., methyl, butyl, decyl; alkoxy, e.g., methoxy, ethoxy, pentyloxy; aklythio, e.g., methylthio, propylthio, heptylthio; dialkylamino, e.g., dimethylamino, diethylamino, dihexylamino; alkoxycarbonyl, e.g., methoxycarbonyl, propoxycarbonyl, nonoxycarbonyl; carboxyacyl, e.g., acetyl, butyryl; carboxamido, e.g., benzamido, aetamido; nitro; fluoro; cyano and the like. Chlorine, bromine and iodine can also be substituents on aromatic portions of carboxyacylating agents.

Examples of suitable anhydrides which can be reacted as the carboxyacylating reagents are acetic anhydride, propionic anhydride, butyric anhydride, isobutyric anhydride, acrylic anhydride, crotonic anhydride, cyclohexane-carboxylic anhydride, benzoic anhydride, napthoic anhydride, furoic anhydride and the like, as well as the corresponding anhydrides substituted with one or more of the above-mentioned substituents. Examples of suitable acid chlorides are acetyl chloride, propionyl chloride, butyryl chloride, isobutyryl chloride, decanoyl chloride, acryloyl chloride, crotonoyl chloride, cyclohexanecarbonyl chloride, 3-cyclohexenecarbonyl chloride, phenylacetyl chloride, succinyl chloride, benzoyl chloride, naphthoyl chloride, furoyl chloride, ethyl oxalyl chloride, ethyl chloroformate, 3-pyridinecarbonyl chloride, phthaloyl chloride and the like, as well as the corresponding acid chlorides substituted with one or more of the above-mentioned substituents.

At least one molecular equivalent of carboxyacylating agent should be used for the introduction of each carboxyacyl moiety. When reactive carboxyacylating agents such as acetic anhydride are used, a diacyl compound is usually obtained even with only one molecular equivalent of carboxyacylating agent. In such cases, some of the amine groups on the B moieties do not form carboxyacylates.

The carboxyacylation usually takes place rapidly in the range of −20° to about +50° C. Suitable diluents are ethers; e g., diethyl ether or tetrahydrofuran; ketones, e.g., acetone or methylethyl ketone; esters, e.g., methyl acetate or ethyl acetate; acetonitrile; pyridine and the like. The desired carboxyacylate often separates from the reaction mixture in crystalline form and can be separated in the usual manner; for example, by filtration or centrifugation. Alternatively, the diluent can be evaporated, preferably at reduced pressure. The carboxyacylates can be purified by conventional techniques; for example, by recrystallization from a suitable solvent or mixture of solvents.

USE IN HAIR GROWTH PROMOTION

The novel compounds of the invention as described above, as well as the two similar compounds described by Catto, et al., are relatively weak and non-toxic when administered orally as antihypertensive agents. It has been unexpectedly discovered that the subject compounds, when applied topically to mammalian skin, in an effective amount, can stimulate or improve the rate of hair growth and prolong the anagen phase of the hair cycle. Moreover, these compounds can be used in high concentrations in topical solutions and can be effective in treatment of alopecia. Typically, these compounds are useful as the active ingredients of different types of preparations such as lotions, solutions, ointments, creams, sprays and the like.

Moreover, the compounds of the present invention which form the active ingredients in the hair treatment preparations can be used in combinations with retinoids as described in my published PCT patent applications Ser. No. US81/00338 (WO82/02833) and US82/01593 (WO83/02558), in that these combinations can exhibit synergism. The combinations can improve or stimulate the rate of hair growth to a greater extent than the individual active ingredients of the combinations alone. Suitable retinoid active ingredients for use in this invention include, for example, derivatives of retinoic acid which have been described in PCT applications US81/00338 and US82/01593, the disclosures of which are incorporated herein by reference.

Preparations such as lotions, creams, conditioners, and the like, including the aforementioned compounds as the active ingredients, can be applied topically to the skin for stimulating or improving the rate of hair growth. It has surprisingly been discovered that the compounds of the present invention are not very toxic, in comparison with minoxidil, and when applied topically to the skin in high concentration have excellent penetration and a long lasting effect, in producing hair growth in an animal model for androgenetic alopecia. Furthermore, retinoids in combination with the subject compounds of this application can exhibit synergism in the animal model studied.

The term "topical" as employed herein, relates to the use of the above compounds, incorporated in a suitable pharmaceutical carrier, and applied at the site of baldness for exertion of local action. Accordingly, such topical compositions include those pharmaceutical forms in which the compound is applied externally by contact with the skin surface to be treated. Conventional pharmaceutical forms for this purpose include ointments, lotions, pastes, jellies, sprays, aerosols, and the like. The term "ointment" embraces formulations (including creams) having oleaginous, absorptive, water-soluble and emulsion-type bases; e.g., petrolatum, lanolin, polyethyene glycols, as well as mixtures of these.

The percentage by weight of the compounds of the invention utilized preferably ranges from about 1% to about 20% of the pharmaceutical preparations; the aforesaid pharmaceutical carriers for topical application constitute a major amount of the preparation.

The active compounds may also be used in a free flowing bead formulation by entrapment with a syneresis-free polymeric network which is hydrophobic. Loading as great as 60–80% should be achieved within the polymeric lattice. In this matrix the functional hair growth agent is held by microsorption and protected from hydrolysis and other modes of decomposition, providing prolonged shelf-life and in a form superior to an emulsion.

In this manner it is possible to hold the functional materials under controlled conditions for availability on demand. This system offers the advantage that retinoids, see PCT US82/01593, can be incorporated as additional functional materials, within a similar polymeric network. The structural integrity of the polymer matrix can be disrupted by mechanical stress or force such as rubbing on application to produce a continuous film of the released active component. This protection is particularly important when one or more of the active ingredients has a short half-life, in the absence of encapsulation and upon release.

The pharmaceutical compositions contemplated by this invention include pharmaceutical compositions suited for topical and systemic action.

The following Examples illustrate the administration vehicles for the present invention. The methods of administration may vary by lotion, cream, ointment, polymeric beadlets, supplement to chow, coating for seeds, etc. These Examples are only meant to be illustrative and do not limit the mode of administration nor the ingredients which can be admixed to the present invention, nor the amount which may be used.

EXAMPLE 1

Lotion Formulation for Topical Administration

| Ingredients | Wt. Percent |
|---|---|
| All-trans retinoic acid | 0.1 |
| N,N-bis[6-(2,4-diaminopyrimi-dinyl-3-N-oxide)]piperazine | 10.0 |
| Ethanol | q.s. to 100.0 |
| Propylene glycol | 15.0 |
| Butylated hydroxytoluene | 0.1 |
| Water | 20.0 |

EXAMPLE 2

Cream Conditioner for Topical Administration

| Ingredients | Wt. Percent |
|---|---|
| 13-cis retinoic acid | 1.0 |
| N,N-bis[4-(2,6-diamino-N-1-oxo-triazinyl)]piperazine | 10.0 |
| Distilled Water | q.s. to 100.0 |
| Cetrimonium Chloride | 5.0 |
| Cetyl alcohol | 4.0 |
| Ethanol | 4.0 |
| Butylated hydroxytoluene | 1.0 |
| Hydrolyzed animal protein | 0.5 |
| Methylparaben, propylparaben | 0.1 |
| Stabilizer | 0.1 |

EXAMPLE 3

Ointment for Topical Administration

All-trans tetinoic acid (0.1 gram) and 10 grams of N,N-bis[6-(2,4 diaminopyrimidinyl-3-N-oxide]piperazine are dissolved in 100 ml of acetone, and the solution admixed with 900 grams of USP grade hydrophilic ointment to a uniform consistency; one gram of butylated hydroxytoluene is added. The water washable cream ointment thus prepared consists of 0.1% retinoic acid and 10% of the N,N-substituted piperazine.

EXAMPLE 4

Polymeric beadlets for Topical Administration

| Ingredients | Amount |
|---|---|
| N,N-bis[6-(2,4 diaminopyrimidinyl-3-N-oxide)]piperazine | 10 gram |
| all-trans retinoic acid | 25 mg. |
| Emolient Base | 100 ml. |

The active ingredients in this example are entrapped within an acrylate copolymer. The hydrophobic polymer is plasticized by most entrapped ingredients. The degree of plasticization determines whether the beads are soft, spreadable, and film-forming with minimal pressure or hard with the ability to withstand shearing of light intensity.

HAIRGROWTH DATA

A rodent model of hypotrichosis has been developed which is useful as an animal model of androgenetic alopecia. The model displays some of the characteristics of male pattern alopecia in humans.

Extreme hair loss is developed after puberty in males. It is typified by initial hair loss on the crown of the head, continuing to the development of hypotrichosis in these animals, as shown by fewer and smaller hair follicles and greatly enlarged sebaceous glands, especially over the crown of the head and the shoulders and upper back. The limbs tend to remain hairy. The females eventually develop male pattern alopecia but not to the same degree as the males.

On topical application of the active compounds of the invention in up to a 20% concentration in a solution of 20% propylene glycol, 60% ethanol and 20% water, a decrease in hair loss was observed. A significantly prolonged anagen phase of the hair cycle was observed, associated in a dose response fashion with the topical application of the active compound. An increase in the amount of hair and an increased rate of hair growth were also associated with the topical administration of the active compounds as measured by microscopic measurement of the outgrowth of hair after bleaching or dyeing the hair.

Increases in the rate of hair growth and the amount of hair growth varied with the topical application of the compounds. The active compounds caused an increase of more than 25% in the amount of hair growth found over the amount of growth found in animals treated with the placebo lotion.

The unexpected novel advantages to be gained from the use of the instant invention are: improved solubility and improved stability and activity of active compounds and the increased percutaneous absorption leading to longer action of compounds; the excellent penetration of skin is due in part to the hydrophilic and lipophilic substituents; and compatability of compounds with non-polar solvents useful for the preservation of the polar groups while in contact with the skin. Furthermore, the less-toxic nature of these compounds allows a greater concentration of the active compound to be applied topically without unwanted side effects.

Although preferred embodiments have been described and various modifications thereto suggested, the invention is not limited to the preferred embodiments or the suggested modifications, but is rather defined by the accompanying claims.

I claim:

1. A compound of the formula:

$$RB_n \qquad (I)$$

wherein R is a multi-functional amine moiety having at least n amine-functional nitrogen sites, n equals 2 to about 8, and B are disubstituted heterocyclic N-oxide moieties which are attached to amine-functional nitrogen atoms of R, and each B is independently selected from the group consisting of pyridines, pyrimidines and triazines, but when R is

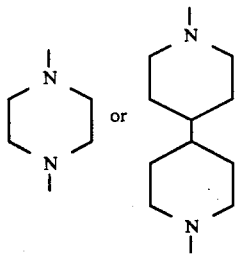

at least one B is not 2,4-diamino-pyrimidine-3-N-oxide.

2. A compound according to claim 1 wherein R is an amine in which the amine-functional nitrogen atoms are members of one or more heterocyclic rings.

3. A compound according to claim 1 wherein R is a moiety in which the amine-functional nitrogen atoms are amino substituents on an aliphatic, aromatic or heterocyclic ring or rings.

4. A compound according to claim 1 wherein R contains at least two amine-functional nitrogen atoms, n equals 2 to 5, and each of the unsubstituted nitrogen bonds on R can be substituted with B or A, where A is hydrogen, alkyl, alkenyl, alkoxyalkyl, cycloalkyl, aryl, alkaryl, aralkyl, alkoxyaralkyl, haloaralkyl, alkylphenylthio, and halaphenylthio.

5. A compound according to claim 1 where B is a moiety of the formula:

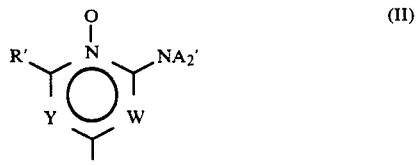

(II)

wherein W and Y are nitrogen or carbon and are the same or different; each A' is independently selected from the group consisting of hydrogen, alkyl, alkenyl, alkoxyalkyl, cycloalkyl, aryl, aralkyl, alkaryl, alkaralkyl, alkoxyaralkyl, haloaralkyl and carboxyacyl; R' is selected from A' and $NA'_2$ wherein A' is as defined above.

6. A compound according to claim 5 wherein both A' are hydrogen and R'=$NH_2$.

7. A compound according to claim 5 wherein R'=$NA'_2$, and one A' on each amine group is hydrogen and the other is carboxyacyl.

8. A compound according to claim 5 wherein W and Y are both carbon, both A' are hydrogen, and R' is $NH_2$.

9. A compound according to claim 5 wherein W and Y are both nitrogen, both A' are hydrogen, and R' is $NH_2$.

10. A compound according to claim 7 wherein one of W and Y is nitrogen.

11. A compound according to claim 10 wherein B is a dicarbamate.

12. A compound according to claim 10 wherein B is a dioxamate.

13. A method of increasing the rate of hair growth on live mammalian skins which comprises topically applying to the skin a composition comprising a compound of the formula:

$$RB_n$$

wherein R is a multifunctional amine moiety having at least n amine-functional nitrogen sites, n equals 2 to about 8, and B are disubstituted heterocyclic N-oxide moieties which are attached to amine-functional nitrogen atoms of R, and each B is independently selected from the group consisting of pyridines, pyrimidines and triazines, said composition being applied in an amount effective to increase the rate of growth of the mammalian hair.

14. A compound according to claim 13 wherein R is an amine in which the amine-functional nitrogen atoms are members of one or more heterocyclic rings.

15. A compound according to claim 13 wherein R is a moiety in which the amine-functional nitrogen atoms are amino substituents on an aliphatic, aromatic or heterocyclic ring or rings.

16. A compound according to claim 13 wherein R contains at least two amine-functional nitrogen atoms, n equals 2 to 5, and each of the unsubstituted nitrogen bonds on R can be substituted with B or A' where A is hydrogen, alkyl, alkenyl, alkoxyalkyl, cycloalkyl, aryl, alkaryl, aralkyl, alkoxyaralkyl, haloaralkyl, alkylphenylthio, and halaphenylthio.

17. A compound according to claim 13 where B is a moiety of the formula:

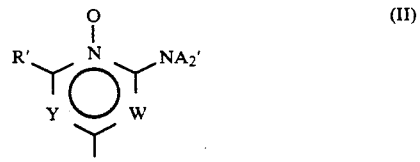

(II)

wherein W and Y are nitrogen or carbon and are the same or different; each A' is independently selected from the group consisting of hydrogen, alkyl, alkenyl, alkoxyalkyl, cycloalkyl, aryl, aralkyl, alkaryl, alkaralkyl, alkoxyaralkyl, haloaralkyl and carboxyacyl; R' is selected from A' and $NA'_2$ wherein A' is as defined above.

18. A compound according to claim 17 wherein both A' are hydrogen and R'=$NH_2$.

19. A compound according to claim 17 wherein R'=$NA'_2$, and one A' on each amine group is hydrogen and the other is carboxyacyl.

20. A method according to claim 13 wherein said composition also contains a retinoid.

* * * * *